(12) United States Patent
King

(10) Patent No.: US 6,811,993 B2
(45) Date of Patent: Nov. 2, 2004

(54) DIAGNOSTIC AND SCREENING METHODS BASED ON MONOCYTE PKC ACTIVITY

(75) Inventor: George L. King, Dover, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 0 days.

(21) Appl. No.: 10/027,204

(22) Filed: Dec. 21, 2001

(65) Prior Publication Data

US 2002/0098533 A1 Jul. 25, 2002

Related U.S. Application Data

(60) Provisional application No. 60/257,769, filed on Dec. 22, 2000.

(51) Int. Cl.[7] .................................................. C12Q 1/48
(52) U.S. Cl. .......................................... 435/15; 435/29
(58) Field of Search ...................... 435/15, 29; 514/866

(56) References Cited

U.S. PATENT DOCUMENTS 5,776,685 A    7/1998  Riedel ............................ 435/6

OTHER PUBLICATIONS

Ceolotto G. Protein Kinase C Activity is Acutely Regulated by Plasma Glucose Concentration in Human Moncytes in Vivo. Diabetes 48(6) 1316–1322, Jun. 1999.*
Kontny et al., "Rottlerin, a PKC isozyme–selective inhibitor, . . . " J Leukoc Biol 2000 Feb;67(2):249–58.
Aleksandrovski, Y., "Molecular mechanisms of Biabetic Complications", Nov. 1998, Biochemistry (Moscow), 63(11); 1249–1257.
Koya et al., "Protein Kinase C Activation . . . ", Jun. 1998, Diabetes, 47(6);859–866.
Ways et al., "Glucotoxicity: a role for protein . . . ", 2000, Diabetes, Current Perspectives;563–564.

* cited by examiner

*Primary Examiner*—Ralph Gitomer
(74) *Attorney, Agent, or Firm*—Fish & Richardson P.C.

(57) ABSTRACT

The invention features a method for evaluating PKC activity in vascular tissues. The invention also features methods for diagnosing cardiovascular and diabetes related disorders, and for identifying and evaluating treatments for cardiovascular or diabetes related disorders. Methods for identifying and evaluating treatments for aging are also included. The methods include measuring PKC activity in monocytes as a surrogate for PKC activity in other tissues.

7 Claims, 4 Drawing Sheets

DIAGNOSTIC AND SCREENING METHODS BASED ON MONOCYTE PKC ACTIVITY

RELATED APPLICATIONS

This application claims the benefit of Provisional Application No. 60/257,769, filed Dec. 22, 2000, the contents of which are incorporated herein by reference, in their entirety.

BACKGROUND

Recent studies have identified that hyperglycemia induces de novo diacylglycerol (DAG) synthesis and activates Protein Kinase C (PKC), which leads to many kinds of vascular abnormalities involving abnormalities of the retina, glomeruli and cardiovascular tissues. In clinical assessment, measurement of PKC activity in vascular tissues is desired, but it is not easy to obtain vascular samples from diabetic patients repeatedly.

SUMMARY OF THE INVENTION

The inventor has discovered that PKC activity, e.g., PKCβ activity, in mononuclear cells, e.g., monocytes, correlates with PKC activity in other tissues, e.g., in vascular or cardiovascular tissue (e.g., in retinal, kidney or aorta vascular tissues or heart). Accordingly, the invention features a method of evaluating the level of PKC activity in a tissue other than monocytes of a subject, e.g., in vascular or cardiovascular tissue, e.g., in retinal, kidney or aorta vascular tissues or heart. The method includes evaluating the level of the PKC activity, e.g., PKC β activity, in mononuclear cells, e.g., monocytes, of the subject. The level of PKC activity in mononuclear cells is correlated with the level of PKC activity in other tissues, e.g., vascular tissue, e.g., in retinal, kidney or aorta vascular tissue or in heart. The subject can be a human, or any non-human animal, e.g., a non-human mammal, e.g., rodent, e.g., a mouse or a rat.

In a preferred embodiment, PKCβ activity is evaluated.

In a preferred embodiment, the subject is a human.

In a preferred embodiment, the subject is an experimental animal.

The invention also features methods of evaluating a subject, e.g., staging of, evaluating the treatment of, or determining if a subject is at risk for (e.g., has a genetic disposition to), has a symptom of, or is afflicted with, a PKC related disorder, e.g., a disorder described herein, e.g., diabetes, diabetes mellitus, Type I diabetes, Type II diabetes, diabetic retinopathy, proliferative diabetic retinopathy, non-proliferative diabetic retinopathy, diabetic nephropathy, microalbumiuria, proteinuria, renal failure, cardiovascular disorder, hypertension, atherosclerosis, coronary artery spasm, congestive heart failure, coronary artery disease, valvular disease, arrhythmias, cardiomyopathy, aging, or an aging-related disorder. The method includes evaluating the level of PKC activity, e.g., PKC β activity, in mononuclear cells, e.g., monocytes, of the subject. Optionally, the method also includes comparing the level of the PKC activity in monocytes of the subject with a standard, e.g., the level of PKC activity in a control sample, e.g., a non-diabetic subject, a preset value, or a basal activity value.

In some embodiments, the level of the PKC activity in monocytes of a subject correlates with risk of developing a PKC-related disorder, e.g., diabetic retinopathy or another PKC related disorder described herein. For example, the level of PKC activity in monocytes of a subject correlates with a genetic predisposition to a PKC-related disorder, e.g., retinopathy.

In a preferred embodiment, PKCβ activity is evaluated.

In a preferred embodiment, the subject is a human.

In a preferred embodiment, the subject is an experimental animal.

In another aspect, the invention features a method of evaluating a subject for the extent, stage, or severity, of a PKC related disorder, e.g., a disorder described herein, e.g., diabetes, diabetes mellitus, Type I diabetes, Type II diabetes, diabetic retinopathy, proliferative diabetic retinopathy, non-proliferative diabetic retinopathy, diabetic nephropathy, microalbumiuria, proteinuria, renal failure, cardiovascular disorder, hypertension, atherosclerosis, coronary artery spasm, congestive heart failure, coronary artery disease, valvular disease, arrhythmias, cardiomyopathy, aging, or an aging-related disorder. The method includes evaluating the level of PKC activity in monocytes of the subject and, optionally, comparing the level of the PKC activity in monocytes of the subject with a standard, e.g., a preset value, the level of PKC activity in a control sample or subject, or a basal activity value. The level of PKC activity in the monocytes is correlated, preferably positively, with the extent, stage, or severity, of the PKC related disorder.

In a preferred embodiment, PKCβ activity is evaluated.

In a preferred embodiment, the subject is a human.

In a preferred embodiment, the subject is an experimental animal.

In another aspect, the invention features methods of evaluating the effect of a treatment for a PKC related disorder, e.g., diabetes, diabetes mellitus, Type I diabetes, Type II diabetes, diabetic retinopathy, proliferative diabetic retinopathy, non-proliferative diabetic retinopathy, diabetic nephropathy, microalbumiuria, proteinuria, renal failure, cardiovascular disorder, hypertension, atherosclerosis, coronary artery spasm, congestive heart failure, coronary artery disease, valvular disease, arrhythmias, cardiomyopathy, aging, or an aging-related disorder, which includes administering a treatment to a subject and measuring PKC activity, e.g., PKC β activity, in the subject's mononuclear cells, e.g., monocytes. The treatment can be, e.g., administration of a compound, e.g., a protein (e.g., an antibody or a hormone, e.g., insulin), a small molecule, a vaccine, a nucleic acid). The subject can be a human, or a non-human animal, e.g., a rat or a mouse, or an animal model for a disorder described herein, e.g., a NOD mouse and its related strains, BB Rat, Leptin or Leptin Receptor mutant rodents, Zucker Diabetic Fatty (ZDF) Rat, Obese Spontaneously Hypertensive Rat (SHROB, Koletsky Rat), Wistar Fatty Rat, New Zealand Obese Mouse, NSY Mouse, Goto-Kakizaki Rat, OLETF Rat, JCR:LA-cp Rat, Neonatally Streptozotocin-Induced (n-STZ) Diabetic Rats, Sprague-Dawley rat, Rhesus Monkey, *Psammomys obesus* (fat sand rat), C57B1/6J Mouse. The level of PKC activity in the monocytes is correlated with the effect of the treatment. The method can be used, e.g., to evaluate the effect of an experimental treatment, e.g., an experimental compound, or a known treatment, e.g., insulin.

In a preferred embodiment, PKCβ activity is evaluated.

In a preferred embodiment, the subject is a human.

In a preferred embodiment, the subject is an experimental animal.

In yet another aspect, the invention features a method of identifying a compound for treating a PKC related disorder, e.g., diabetes, diabetes mellitus, Type I diabetes, Type II diabetes, diabetic retinopathy, proliferative diabetic retinopathy, non-proliferative diabetic retinopathy, diabetic nephropathy, microalbumiuria, proteinuria, renal failure, cardiovascular disorder, hypertension, atherosclerosis, coronary artery spasm, congestive heart failure, coronary artery disease, valvular disease, arrhythmias, cardiomyopathy, aging, or an aging-related disorder. The method includes administering a test compound to a subject, e.g., an animal, e.g., a mouse or a rat, or an animal model for a disorder described herein, and measuring PKC activity, e.g., PKC β activity, in mononuclear cells, e.g., monocytes, of the subject. The level of PKC activity in the monocytes is correlated with the effect of the treatment. The method may also optionally include identifying a subject in need of a treatment for the PKC related disorder, and comparing the PKC activity, e.g., PKC β activity, in monocytes, after administration of a test compound, to a standard. A compound for the treatment of the disorder is identified when the PKC activity after the administration of the compound is altered, e.g., increased or decreased, as compared to a standard, e.g., a preset value, the level of PKC activity in a control sample, a basal activity value, or the PKC activity before, or in the absence of, the administration of the compound.

In a preferred embodiment, PKCβ activity is evaluated.

In a preferred embodiment, the subject is a human.

In a preferred embodiment, the subject is an experimental animal.

In a preferred embodiment, the method further includes isolating a compound identified as having an effect on a PKC-related disorder, and, optionally, administering the compound to a subject, e.g., a human subject having such a disorder In another aspect, the invention features a method of identifying a compound for the treatment of aging or an aging-related disorder in a subject, e.g., an animal. e.g., a mouse or a rat, or an animal model for a disorder described herein. The method includes administering a test compound to the subject and evaluating a PKC activity, e.g., a PKC β activity, in monocytes of the subject. The level of PKC activity is correlated with the effect of the treatment on the disorder. Preferably, the level of PKC activity is decreased compared to a standard. A compound for the treatment of aging or an aging-related disorder is identified when the PKC activity after the administration of the compound is altered, e.g., increased or decreased, as compared to a standard, e.g., a preset value, the level of PKC activity in a control sample, a basal activity value, or the PKC activity before, or in the absence of, the administration of the compound.

In a preferred embodiment, PKCβ activity is evaluated.

In a preferred embodiment, the subject is a human.

In a preferred embodiment, the subject is an experimental animal.

In a preferred embodiment, the method further includes isolating a compound identified as having an effect on aging or an aging-related disorder, and, optionally, administering the compound to a subject, e.g., a human subject having such a disorder In another embodiment, the invention provides a method of evaluating the effect of a treatment for aging or an aging-related disorder on a subject, which includes administering a treatment for aging or an aging-related disorder to a subject, e.g., a human, or a non-human animal, and evaluating the level of PKC activity, e.g., PKC β activity, in the subject's monocytes.

In a preferred embodiment, PKCβ activity is evaluated.

In a preferred embodiment, the subject is a human.

In a preferred embodiment, the subject is an experimental animal.

The methods described herein can be used, e.g., to evaluate the effect of a treatment on PKC activity before, during, and/or after administration of a treatment. In some embodiments, the effect of a treatment can be evaluated over time (e.g., over minutes, hours, days, weeks, months) by repeating the evaluation of PKC activity as described herein. For example, PKC activity can be evaluated one, two, three, four, five, or more times after the initial evaluation of PKC activity in response to treatment. In other embodiments, the treatment can be administered more than once, and the effect of subsequent administrations can be evaluated by repeating the evaluation of PKC activity in mononuclear cells, e.g., monocytes, as described herein.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
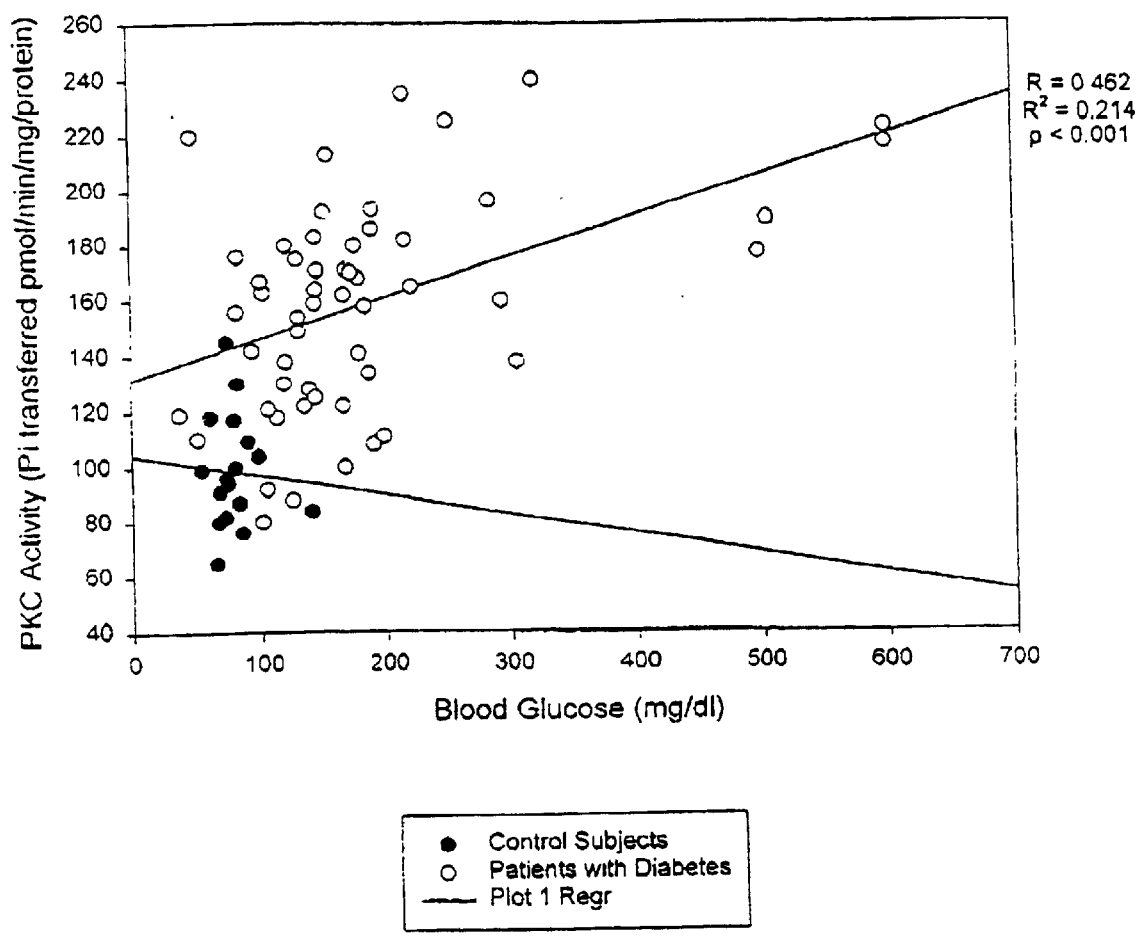
FIG. 1 is a graph showing the correlation between blood glucose level and PKC activity in monocytes.

Leukocytes, especially monocytes, contain PKC α and β isoforms. PKC activation is associated with monocyte adherence to endothelial cells and with their transendothelial migration. The invention is based, in part, on the discovery that PKC activity in cardiovascular tissues, e.g., in vascular tissues of retina or kidney, of subjects, e.g., normal or diabetic subjects, is correlated with PKC activity, e.g., PKC β activity, in mononuclear cells, e.g., monocytes.

Further, the invention is based, in part, on the discovery that PKC activity, e.g., PKC β activity, is correlated with aging, and with severity of diabetic complications, e.g., diabetic nephropathy or diabetic retinopathy.

Preparation of Mononuclear Cells

Mononuclear cells can be prepared, e.g., substantially isolated from other blood components, by various methods known in the art. An exemplary method is described herein below.

Monocytes of rats and also human control subjects and patients with diabetes were isolated from blood with anticoagulant of sodium citrate. The blood sample was put onto the same volume of Histopaque-1077 (Sigma) and centrifuged at 400×g for 30 minutes at room temperature. The layer containing mononuclear cells was transferred to a new tube and washed with phosphate-buffered saline (PBS). After centrifugation at 400×g for 10 minutes, cell pellet was suspended with a solution of 144 mM NH4Cl and 17 mM Tris-HCl, pH 7.65 to lyse the contaminated red blood cells. Mononuclear cells were washed with PBS and used in this study.

In Situ PKC Activity Assay

PKC activity assays are known in the art. One type of assay includes (a) contacting the sample to be evaluated for PKC activity with (i) a substrate molecule capable of accepting a phosphate (e.g. a kinase substrate peptide) and (ii) a labeled source of phosphate (e.g. labeled ATP, e.g. radio labeled ATP); and (b) evaluating the amount of label transferred to the substrate molecule in the presence of the sample. PKC activity can be evaluated, e.g., in situ or in vitro, e.g., in a cellular or tissue membrane fraction. Exemplary methods are described herein below.

Mononuclear cells of human and rats and retina of rats were suspended in a buffer containing 137 mM NaCl, 4.3 mM KCl, 0.3 nM $Na_2HPO_4$, 0.4 mM $KH_2PO_4$, 5.5 mM D-Glucose, 10 mM $MgCl_2$, 1 mM $CaCl_2$, 25 mM β-glycerophosphate, and 20 mM HEPES, pH 7.2. The reaction was initiated by adding solution containing digitonin, substrate peptide, (RKRTLRRL, corresponding to the epidermal growth factor receptor), and $\gamma$-$^{32}$P-ATP. After 15 minutes incubation at room temperature, the reaction was terminated with trichloroacetic acid (TCA). An aliquot of the reaction solution was spotted on a phosphocellulose paper, and the paper was washed with 75 mM phosphoric acid solution, followed by washing with 75 mM sodium phosphate solution to remove residual $\gamma$-$^{32}$P-ATP. The paper was put into a scientillation vial and radioactivity of $^{32}$p was assayed by scientillation counter. The paper was put into a scintillation vial and radioactivity of $^{32}$p incorporated into substrate peptide per minute per mg of protein, and calculated by the difference between the activity in the presence of substrate peptide and the activity in the absence of the peptide.

PKC Activity in the Membranous Fraction

After isolating membranous fractions of heart and aorta of rats, PKC activity was measured by its ability to transfer $^{32}$P from $\gamma$-$^{32}$P-ATP into specific substrate peptide (same peptide used in the in situ assay) in the presence of $Ca^{2+}$, Phosphatidylserine (PS), and DAG. PKC activity was calculated by subtracting the nonspecific activity in the absence of $Ca^{2+}$, PS, DAG, and expressed as pmol of $^{32}$P incorporated into substrate peptide per minute per mg of protein.

Data Analysis

The differences were analyzed by one way ANOVA test. Linear regression was assessed using a linear fit with Sigma Stat version 2.03 statistical software.

Rat Studies

Male Sprague-Dawley rats at the age of 6 weeks were used in this study. Diabetic rats were induced by intraperitoneal injection of STZ (60 mg/kg). Some of the STZ-induced diabetic rats were treated with insulin (insulin pellet, inserted subcutaneously) or oral PKC β inhibitor (LY333531). After 2 weeks, mononuclear cells from blood sample, heart, aorta and retina were isolated from the rats. PKC activity in these tissues was measured as described below.

PKC activities in heart, aorta and retina of rats were tested to compare with PKC activity in mononuclear cells. As compared to the control rats, PKC activities in heart, aorta and retina were increased by 42%, 50%, 51%, respectively. PKC activity in rat mononuclear cells was significantly increased in STZ-induced diabetic rats (56% increase). The increase in PKC activity was restored to the level of control rats by insulin.

Human Studies

PKC activity was measured in monocytes of normal (non-diabetic) human subjects. Monocyte PKC activity was found to decrease with the age of the subjects. PKC activity in older subjects (age 40 or greater) was substantially less than that in younger subjects.

Figure 2:
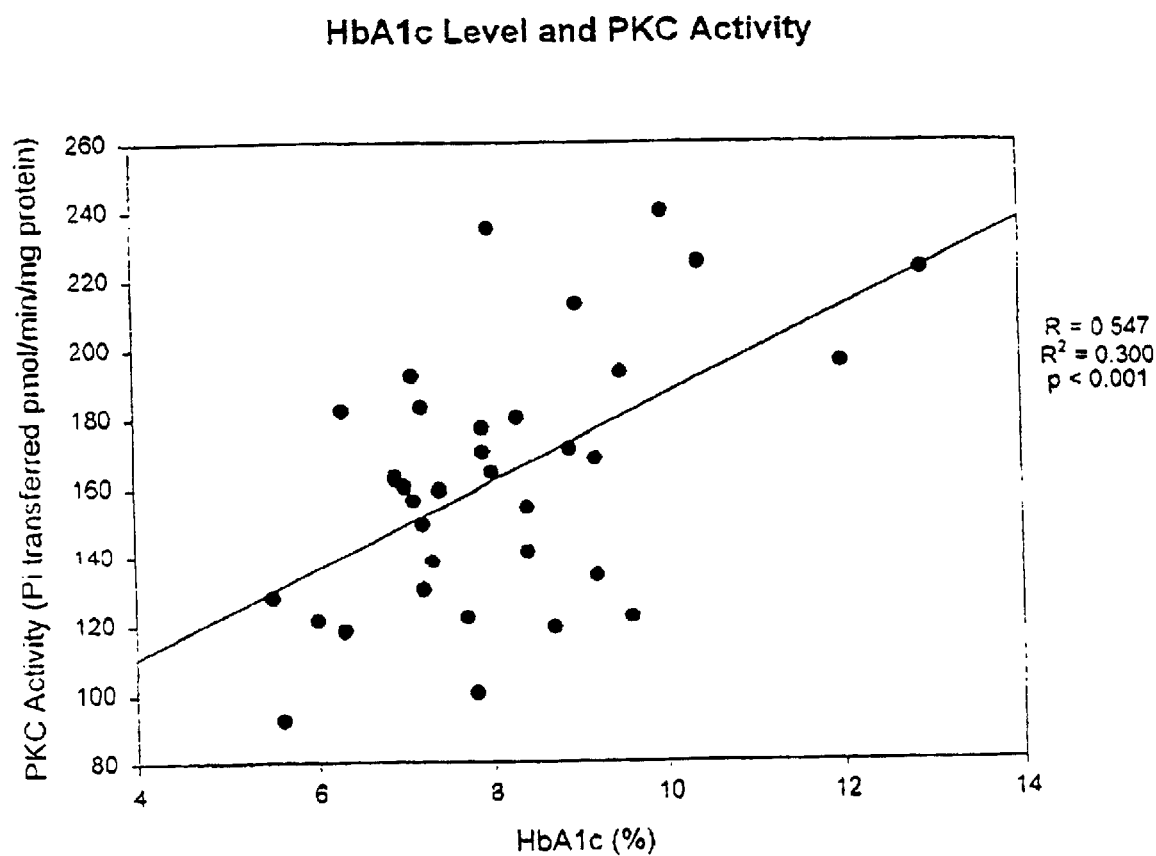
FIG. 2 is a graph showing the correlation between hemoglobin A1c (HbA1c) level and PKC activity in monocytes. In the blood, glucose binds irreversibly to hemoglobin molecules within red blood cells. The amount of glucose that is bound to hemoglobin is directly tied to the concentration of glucose in the blood. Thus, measuring the amount of glucose bound to hemoglobin can provide an assessment of average blood sugar control during the 60 to 90 days prior to the test. The HbA1c test is the most common test for glycated hemoglobin.

PKC activity in human monocytes was significantly increased by 62% in patients with diabetes compared to control subjects (p<0.05). PKC activity in human mononuclear cells was significantly correlated with blood glucose level (R=0.462, $R^2$=0.214, p<0.001) (FIG. 1), and with levels of glycosylated hemoglobin (HbA1c) in the subjects (R=0.547, $R^2$=0.300, p<0.001) (FIG. 2).

Figure 3:
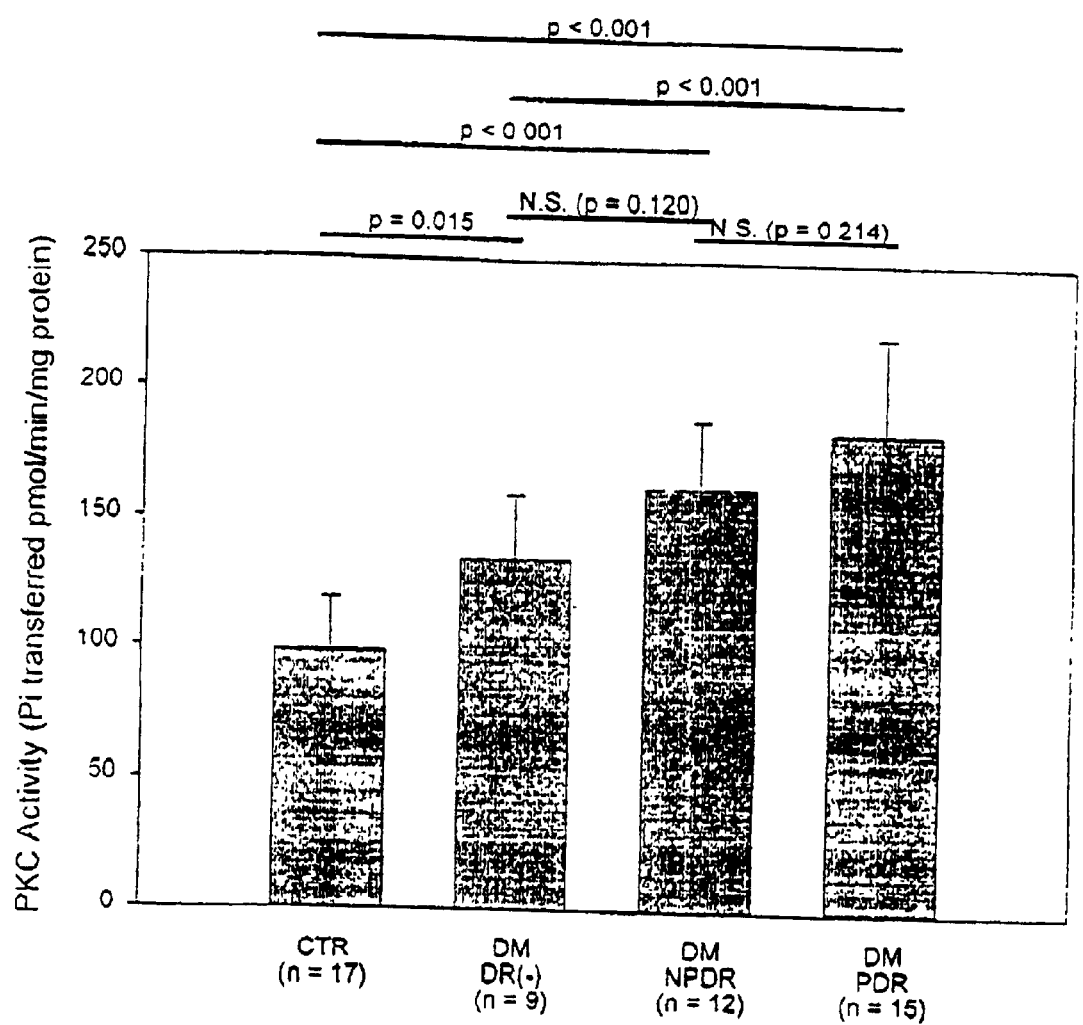
FIG. 3 is a graph showing the correlation between diabetic retinopathy and PKC activity in monocytes of diabetic patients.

To examine relationships between PKC activity and diabetic complications, the diabetic patients were divided into groups according to the severity of complications. PKC activity increased with severity of diabetic retinopathy (non-DR; 134±24, non-proliferative-DR; 162±25, proliferative DR; 184±37) (FIG. 3). Also, PKC activity in the group of diabetic patients with proliferative retinopathy was significantly higher than that in the group of patients without retinopathy (p<0.001).

Figure 4:
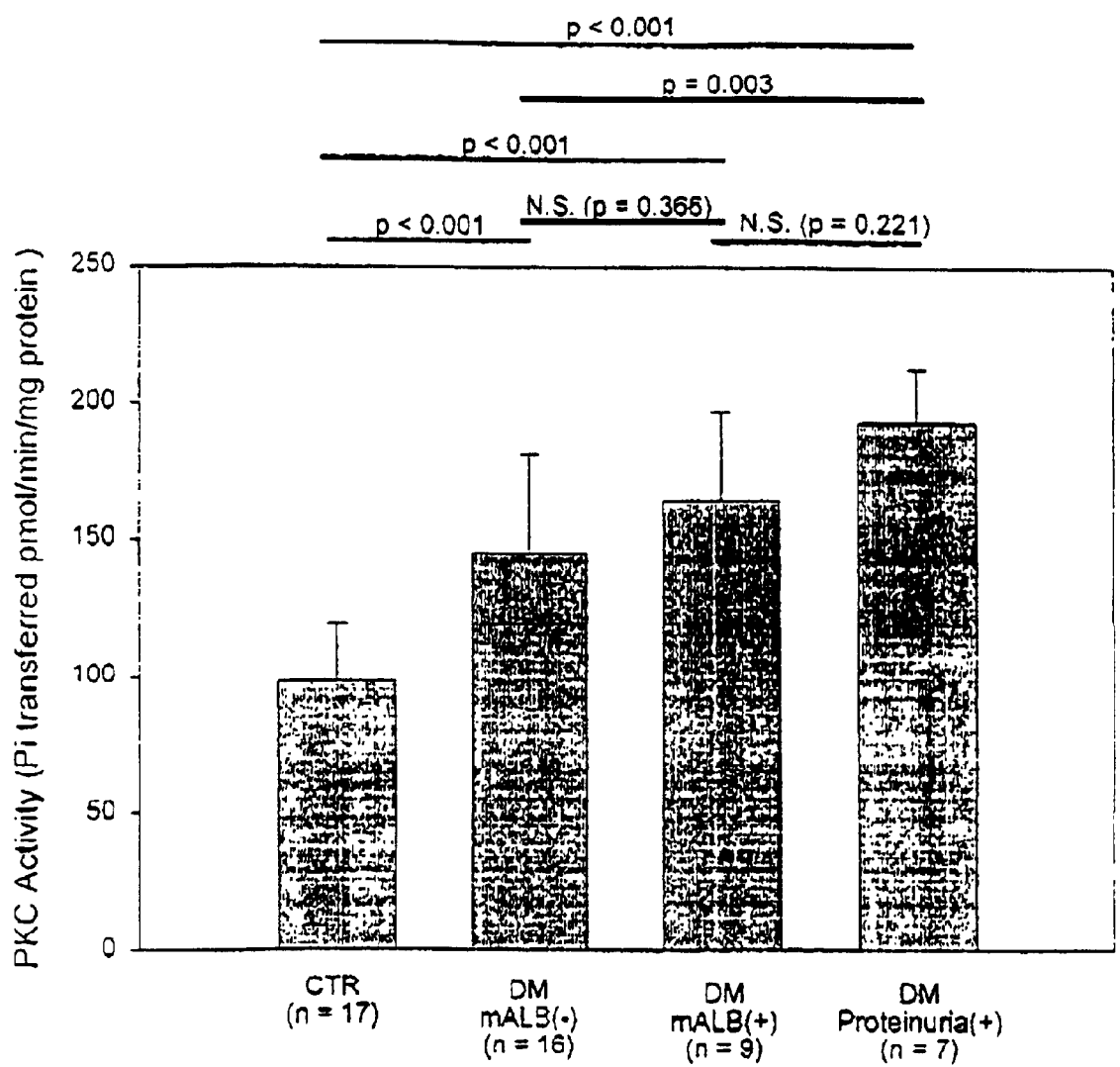
FIG. 4 is a graph showing the correlation between diabetic nephropathy and PKC activity in monocytes of diabetic patients.

Patients were also classified according to severity of diabetic nephropathy. PKC activity was increased in correlation with the severity of the nephropathy (without microalbumiuria; 145 ±35, with microalbumiuria; 164±31, with proteinuria and/or renal failure; 192±19), and a significant difference was identified between the diabetic group without microalbumiuria and the group with proteinuria and/or renal failure (p=0.003) (FIG. 4). Analysis of the data also indicates that PKC activity in monocytes has significance with regard to the genetics of disease, e.g., in retinopathy. PKC activity correlated with a disposition (which can be, e.g., a genetic predisposition), to earlier development of PKC related disease, e.g., retinopathy.

As shown above, the level of PKC activity in monocytes was correlated with age in normal subjects, suggesting that monocyte PKC activity can be used as an indicator for aging or symptoms of aging. Therefore, monocyte PKC activity may be used as an assay in the diagnosis, and in the identification and evaluation of treatments, for aging or aging related disorders and symptoms.

Also, PKC activity in mononuclear cells was correlated with that in heart, aorta, and retinal vasculature, indicating that PKC activity in mononuclear cells can be used as a surrogate marker for PKC activation in vascular and heart tissues. Therefore, monocyte PKC activity can be used as an assay for the diagnosis (including diagnosis of disease stage, severity, or predisposition) of cardiovascular disorders, and the identification and evaluation of treatment for cardiovascular disorders. Examples of cardiovascular disorders or disorders involving the heart include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include retinopathy, hypertension, atherosclerosis, coronary artery spasm, congestive heart failure, coronary artery disease, valvular disease, arrhythmias, and cardiomyopathies.

In addition, PKC activity in mononuclear cells of human subjects was correlated with glycemic control and associated with the severity of diabetic complications, suggesting that PKC activity in monocytes can serve as a surrogate for evaluation of diabetic complications. Examples of diabetic complications include, but are not limited to, diabetic nephropathy, diabetic retinopathy, altered or deficient blood glucose level or glycosylated hemoglobin.

A number of embodiments of the invention have been described. Nevertheless, it will be understood that various modifications may be made without departing from the spirit and scope of the invention. Accordingly, other embodiments are within the scope of the following claims.

What is claimed is:

1. A method of evaluating a subject for the extent, stage, or severity, of a cardiovascular complication of diabetes, the method comprising:

determining the level of PKC activity in monocytes of the subject;

optionally comparing the level of the PKC activity in monocytes of the subject with a standard, and correlating the level of PKC activity with the extent, stage, or severity, of the cardiovascular complication of diabetes.

2. The method of claim 1, wherein the diabetic complication is diabetic retinopathy.

3. The method of claim 1, wherein the diabetic complication is diabetic nephropathy.

4. The method of claim 1, wherein the diabetic complication is hypertension, atherosclerosis, coronary artery spasm, congestive heart failure, coronary artery disease, valvular disease, arrhythmias or cardiomyopathy.

5. The method of claim 1, wherein the PKC activity is PKC β activity.

6. The method of claim 1, wherein the subject is a human.

7. The method of claim 1, wherein the subject is an experimental animal.

* * * * *

UNITED STATES PATENT AND TRADEMARK OFFICE
CERTIFICATE OF CORRECTION

PATENT NO. : 6,811,993 B2
DATED : November 2, 2004
INVENTOR(S) : George Liang King It is certified that error appears in the above-identified patent and that said Letters Patent is hereby corrected as shown below:

<u>Column 1,</u>
Line 8, insert following paragraph:

-- FEDERALLY SPONSORED RESEARCH OR DEVELOPMENT

This invention was made with government support under Grant Number EY5110 awarded by The National Institutes of Health. The government has certain rights in the invention. --.

Signed and Sealed this

Fourth Day of April, 2006

JON W. DUDAS
*Director of the United States Patent and Trademark Office*